(12) United States Patent
Tanaka et al.

(10) Patent No.: US 9,029,293 B2
(45) Date of Patent: May 12, 2015

(54) TOBACCO AXILLARY BUD INHIBITOR AND TOBACCO AXILLARY BUD-INHIBITING METHOD

(75) Inventors: Motoki Tanaka, Ibaraki (JP); Keijitsu Tanaka, Ibaraki (JP); Takeshi Shibuya, Ibaraki (JP); Eiji Ikuta, Tokyo (JP); Kotaro Yoshinaga, Tokyo (JP); Yuki Yamaguchi, Ibaraki (JP)

(73) Assignee: SDS Biotech K.K., Tokyo (JP)

( * ) Notice: Subject to any disclaimer, the term of this patent is extended or adjusted under 35 U.S.C. 154(b) by 0 days.

(21) Appl. No.: 14/125,681

(22) PCT Filed: Jun. 13, 2011

(86) PCT No.: PCT/JP2011/063448
§ 371 (c)(1),
(2), (4) Date: Dec. 12, 2013

(87) PCT Pub. No.: WO2012/172621
PCT Pub. Date: Dec. 20, 2012

(65) Prior Publication Data
US 2014/0121112 A1    May 1, 2014

(51) Int. Cl.
*A01N 43/40* (2006.01)
*A01N 57/18* (2006.01)
*A61K 31/44* (2006.01)
*A61K 31/16* (2006.01)
*A01N 37/18* (2006.01)
*A01N 43/78* (2006.01)

(52) U.S. Cl.
CPC ............... *A01N 43/40* (2013.01); *A01N 37/18* (2013.01); *A01N 43/78* (2013.01)

(58) Field of Classification Search
None
See application file for complete search history.

(56) References Cited

U.S. PATENT DOCUMENTS

| 3,640,699 A | 2/1972 | Horrom et al. |
| 3,672,866 A | 6/1972 | Damiano et al. |
| 3,707,366 A | 12/1972 | Cahoy et al. |
| 4,046,809 A | 9/1977 | Wilcox |
| 4,123,250 A | 10/1978 | Kupelian |
| 4,685,951 A | 8/1987 | Nishimuta et al. |
| 4,692,184 A | 9/1987 | Lee |
| 4,988,384 A | 1/1991 | Sing et al. |
| 2010/0234226 A1* | 9/2010 | Hacker et al. ................. 504/134 |

FOREIGN PATENT DOCUMENTS

| CN | 1256615 A | 6/2000 |
| JP | 53-43569 B | 11/1978 |
| JP | 61-158904 A | 7/1986 |
| JP | 61158904 * | 7/1986 |
| JP | 61-158904 A | 10/1986 |
| JP | 62-298503 A | 12/1987 |
| JP | 62-298504 A | 12/1987 |
| JP | 62298503 * | 12/1987 |
| JP | 62298504 * | 12/1987 |
| JP | 2-142780 A | 5/1990 |
| JP | 2142780 * | 5/1990 |
| JP | 3-167164 A | 7/1991 |
| JP | 4-47667 B2 | 8/1992 |
| JP | 447667 A | 8/1992 |
| JP | 6-60171 B2 | 8/1994 |
| JP | 660171 B | 8/1994 |
| WO | 98/51148 A1 | 11/1998 |

OTHER PUBLICATIONS

English translation of the International Preliminary Report on Patentability and Written Opinion of the International Searching Authority issued Dec. 17, 2013 for International Application No. PCT/JP2011/063448.

M. Fujiyama et al., "New Herbicide Dithiopyr", Agrochemicals, vol. 30, Issue 1, 1991.

* cited by examiner

*Primary Examiner* — Alton Pryor

(74) *Attorney, Agent, or Firm* — Sughrue Mion, PLLC

(57) ABSTRACT

An inhibitor for tobacco axillary bud growth, the inhibitor containing one or more cell division inhibitors selected from pyridine-based compounds and benzamide-based compounds. This inhibitor may further include an aliphatic alcohol having 6 to 20 carbon atoms in combination with the one or more cell division inhibitors.

4 Claims, No Drawings

TOBACCO AXILLARY BUD INHIBITOR AND TOBACCO AXILLARY BUD-INHIBITING METHOD

CROSS REFERENCE TO RELATED APPLICATIONS

This is a National Stage of International Application No. PCT/JP2011/063448 filed Jun. 13, 2011, the contents of which are incorporated herein by reference in their entirety.

TECHNICAL FIELD

The present invention relates to an inhibitor for tobacco axillary bud growth and a method for inhibiting tobacco axillary bud growth.

BACKGROUND ART

A labor for removing axillary buds just before harvesting of tobacco is necessary for securing the yield and quality of leaf tobacco. However, in order to perform the labor by hand work, a huge amount of work is required. Therefore, nowadays, a method involving spraying an inhibitor for tobacco axillary bud growth has been developed and widely used.

As an inhibitor for tobacco axillary bud growth which has been widely used from the Showa 30's (1955-1964), there is known inhibitors including, as an active ingredient, maleic hydrazide or a salt thereof, having a systemic action. The inhibitor is actually used at a concentration as high as about 5,000 ppm and is poor in terms of sustained chemical efficacy. Hence, there has been a problem in that a large amount of the inhibitor is required. Further, hydrazine produced by decomposition of maleic hydrazide exhibits oncogenic potential, and hence use of the inhibitor is currently restricted.

Therefore, in recent years, a contact-type inhibitor for tobacco axillary bud growth, which is sprayed by contact with stem, has been used. As the contact-type inhibitor, there are known, for example, an inhibitor including a saturated aliphatic alcohol as an active ingredient and an inhibitor including a dinitroaniline-based chemical substance as an active ingredient.

The inhibitor for axillary bud growth including a saturated aliphatic alcohol as an active ingredient has a high effect of killing axillary buds by contact. However, the inhibitor including a saturated aliphatic alcohol as an active ingredient is poor in terms of sustained chemical efficacy and requires spraying of the inhibitor at least twice in order to prevent elongation of axillary buds in the later growth period. In addition, attachment of the sprayed inhibitor to leaves at the time of use causes bleaching, another harmful effect of the inhibitor, and reduction in quality of the leaves. Further, as the inhibitor is dropped and accumulated at the base part of a plant, all stem bases are necrotized, resulting in killing the plant.

On the other hand, the inhibitor including a dinitroaniline-based chemical substance as an active ingredient is disclosed in, for example, U.S. Pat. No. 3,672,866 A (Patent Document 1), U.S. Pat. No. 4,046,809 A (Patent Document 2) and U.S. Pat. No. 4,123,250 A (Patent Document 3). The inhibitor including a dinitroaniline-based compound as an active ingredient contains a certain organic solvent. The inhibitor has an effect of stopping growth of axillary buds by dehydrating and necrotizing axillary buds by contact of the dinitroaniline-based chemical substance and the organic solvent with the axillary buds and allowing the above-mentioned chemical substance to be absorbed from the axillary bud plumule part or from wounds after removal of the axillary buds to inhibit cell division and has a high effect of inhibiting formation and elongation of axillary buds.

However, the inhibitor including a dinitroaniline-based chemical substance as an active ingredient has the following problems, for example. The inhibitor sometimes causes harmful effects such as deformation of young leaves of the upper node, lack in expansion, necrosis of mesophyll, damages of the petiole parts of middle or upper leaves, developmental disorders of adventitious roots, and necrosis immediately after spraying; and induces diseases such as hollow heart, crown rot, and gray mold from wound sites formed in the petiole base by the harmful effects to cause adverse effects on the yield and quality of leaf tobacco.

As mentioned above, the inhibitor for axillary bud growth currently used in cultivation of tobacco have many problems yet to be solved from the viewpoint of sustainment of the chemical efficacy and occurrence of harmful effects.

Therefore, an inhibitor for tobacco axillary bud growth which is excellent in terms of sustained chemical efficacy, induces no harmful effect and no disease, and can contribute to improvement in labor productivity has been desired.

A cell division inhibitor of a pyridine-based compound or a benzamide-based compound to be used in the present invention is a known compound, and for example, JP 04-47667 B (Patent Document 4, U.S. Pat. No. 4,692,184), JP 06-60171 B (Patent Document 5, U.S. Pat. No. 4,988,384), U.S. Pat. No. 3,640,699 (Patent Document 6), JP 53-43569 B (Patent Document 7, U.S. Pat. No. 3,707,366) describe that dithiopyr, thiazopyr, propyzamide or tebutam are used as herbicides, respectively. Hitherto, however, the cell division inhibitor of a pyridine-based compound or a benzamide-based compound has not been used as an inhibitor for tobacco axillary bud growth.

In the present invention, the cell division inhibitor means a drug inhibiting cell proliferation by ceasing mitotic division of plant cells.

PRIOR ART

Patent Document

[PATENT DOCUMENT 1] U.S. Pat. No. 3,672,866 A
[PATENT DOCUMENT 2] U.S. Pat. No. 4,046,809 A
[PATENT DOCUMENT 3] U.S. Pat. No. 4,123,250 A
[PATENT DOCUMENT 4] JP 04-47667 B
[PATENT DOCUMENT 5] JP 06-60171 B
[PATENT DOCUMENT 6] U.S. Pat. No. 3,640,699 A
[PATENT DOCUMENT 7] JP 53-43569 B

SUMMARY OF INVENTION

Problem to Solved by the Invention

An object of the present invention is to provide an inhibitor for tobacco axillary bud growth, which shows sustained chemical efficacy at a low concentration, induces no harmful effect and no disease, and can contribute to improvement in labor productivity.

Means to Solve the Problem

The inventors of the present invention have made various studies on many kinds of compounds to develop a novel inhibitor for tobacco axillary bud growth. As a result, the inventors have found that a cell division inhibitor of a pyridine-based compound or a benzamide-based compound can suppress growth of tobacco axillary buds at a low concentration for a long period of time and has no harmful effect on stem and leaf parts of tobacco.

The inventors have further found that, when the cell division inhibitor of a pyridine-based compound or a benzamide-based compound is used in combination with an aliphatic alcohol having 6 to 20 carbon atoms, the effect of inhibiting growth of tobacco axillary buds can be improved synergistically, thus completing the present invention.

The cell division inhibitor of a pyridine-based compound or a benzamide-based compound to be used in the present invention is known as an herbicide, but there is no literature describing use of the synthesis inhibitor as an inhibitor for tobacco axillary bud growth.

The present invention relates to the following inhibitor for tobacco axillary bud growth and method for inhibiting tobacco axillary bud growth.

(1) An inhibitor for tobacco axillary bud growth, including, as an active ingredient, one or more kinds selected from cell division inhibitors of a pyridine-based compound and a benzamide-based compound.

(2) The inhibitor for tobacco axillary bud growth according to (1) above, in which the pyridine-based compound is selected from dithiopyr and thiazopyr.

(3) The inhibitor for tobacco axillary bud growth according to (2) above, in which the pyridine-based compound is dithiopyr.

(4) The inhibitor for tobacco axillary bud growth according to (1) above, in which the benzamide-based compound is selected from propyzamide, tebutam and benzipram.

(5) The inhibitor for tobacco axillary bud growth according to (4) above, in which the benzamide-based compound is propyzamide.

(6) The inhibitor for tobacco axillary bud growth according to any one of (1) to (5) above, further including an aliphatic alcohol having 6 to 20 carbon atoms.

(7) The inhibitor for tobacco axillary bud growth according to (6) above, in which the aliphatic alcohol having 6 to 20 carbon atoms is decyl alcohol, 2-ethyl hexanol or geraniol.

(8) A method for inhibiting tobacco axillary bud growth, including applying the inhibitor for tobacco axillary bud growth according to any one of (1) to (7) above.

Effects of Invention

The inhibitor for tobacco axillary bud growth of the present invention has a high effect of inhibiting axillary bud growth and shows sustained chemical efficacy. Further, the inhibitor has no harmful effects on the stem and leaf parts and the root part. Therefore, in cultivation of tobacco, the inhibitor can achieve an increase in yield, improvement of quality, and improvement of labor productivity by reduction in labor for removing axillary buds.

DESCRIPTION OF EMBODIMENTS

Among the cell division inhibitors to be used in the present invention, specific examples of the cell division inhibitor comprising a pyridine-based compound include dithiopyr and thiazopyr.

Specific examples of the cell division inhibitors comprising a benzamide-based compound include propyzamide, tebutam and benzypram.

In consideration of an effect of inhibiting formation and growth of tobacco axillary buds, dithiopyr is particularly as a pyridine-based compound, and propyzamide is particularly desirabe as a pyridine-based compound.

Further, when the cell division inhibitor of a pyridine-based compound or a benzamide-based compound as mentioned above is blended with an aliphatic alcohol having 6 to 20 carbon atoms, it is possible to synergistically improve an effect of inhibiting growth of tobacco axillary buds and sustainment of the effect.

Examples of the aliphatic alcohol having 6 to 20 carbon atoms to be used in the present invention include acetone glyceryl acetal, ambrinol, α-bisabolol, d-borneol, 1-borneol, 2-butoxyethanol, α-campholenol, 1-carveol, carveol, β-caryophyllene alcohol, cedrenol, cedrol, citral, citronellal, citronellol, 1-citronellol, cyclohexanol, 2-cyclohexylethanol, 2,4-decadienol, 3-decanol, decyl alcohol, 2-decenol, 9-decenol, 4-decenol, dihydrocarveol, 7,8-dihydro-β-ionol, 3,7-dimethyl-6-octen-3-ol, dihydromyrcenol, dihydroperillyl alcohol, 2,5-dimethyl-1,4-dithiane-2,5-diol, 2,6-dimethyl-4-heptanol, 3,7-dimethyl-1,5,7-octatrien-3-ol, 2,6-dimethyl-2-heptanol, 3,6-dimethyl-3-octanol, 2,4-dimethyl-4-nonanol, 2-dodecanol, dodecanol, 2-dodecenol, elemol, 2-ethylbutanol, 2-ethylfenchol, 2-ethylhexanol, farnesol, fenchyl alcohol, geraniol, geranyllinalool, heptadecanol, heptanal glyceryl acetal, 2-heptanol, 3-heptanol, 4-heptanol, heptanol, 1-hepten-3-ol, 2-heptenol, 3-heptenol, cis-4-heptenol, hexadecanol, 2,4-hexadienol, hexanal glyceryl acetal, hexanol, 2-hexanol, 3-hexanol, 4-hexanol, 1-hexen-3-ol, trans-2-hexenal glyceryl acetal, 2-hexenol, 3-hexenol, cis-2-hexenol, cis-3-hexenol, cis-4-hexenol, trans-2-hexenol, trans-3-hexenol, trans-4-hexenol, hydroxycitronellal diethyl acetal, hydroxycitronellol, α-ionol, β-ionol, isoborneol, isodihydrocarveol, isogeraniol, isophytol, isopulegol, isovaleraldehyde glyceryl acetal, lavandulol, 8-p-menthene-1,2-diol, linalool, linanool oxide, 2-p-menthene-1,2-diol, 2,8-p-menthadiene-1-ol, 1,8-p-menthadiene-4-ol, menthadienol, p-menthan-2-ol, p-menthan-7-ol, p-menthan-8-ol, 8-p-menthan-7-ol, 1-menthol, dl-menthol, 3-(menthoxy)-1,2-propanediol, 3-methyl-2-pentanol, 4-methyl-2-pentanol, 6-methyl-3-heptanol, 5-methyl-3-heptanol, 2-methyl-3-hexanol, 3-methyl-3-pentanol, 6-methyl-5-hepten-2-ol, 2-methyl-5-hepten-2-ol, 5-methylhexanol, 2-methylpentanol, 3-methylpentanol, 4-methylpentanol, 3-(methylthio)hexanol, myrcenol, myrtenol, neodihydrocarveol, α-neomenthol, neomenthol, nerol, cis-nerolidol, trans-nerolidol, nerolidol, 2,4-nonadienol, 3,6-nonadienol, trans,cis-2,6-nonadienol, nonadienol, nonanol, 2-nonanol, 3-nonanol, 1-nonen-3-ol, 3-nonenol, 6-nonenol, cis-2-nonenol, trans-2-nonenol, 2,6-dimethyl-5,7-octadien-2-ol, 1,5-octadien-3-ol, octadecanol, 3,5-octadienol, 1,3-octanediol, 2-octanol, 3-octanol, octanol, 1-octen-3-ol, 2-octen-4-ol, 2-octenol, 3-octenol, cis-5-octenol, cis-9-octadecenol, pentadecanol, perillyl alcohol, phytol, pinocarveol, piperitol, rhodinol, α-santalol, sclareol, terpineol, 1-terpineol, 4-terpineol, α-terpineol, β-terpineol, 4-tert-butylcyclohexanol, tetradecanol, tetrahydrocuminol, 3,7-dimethyloctanol, 3,7-dimethyl-2-octanol, 2,6-dimethyl-2-octanol, 3-thujanol, sabinene hydrate, tridecanol, 2-tridecenol, 3,3,5-trimethylcyclohexanol, 3,5,5-trimethylhexanol, 2,4-undecadienol, 2-undecanol, undecanol, cis,cis-1,5,8-undecatrien-3-ol, 10-undecenol, 2-undecenol, verbenol, vetiverol, viridiflorol, 3-1-menthoxy-2-methylpropane-1,2-diol, citral glyceryl acetal, menthone 1,2-glyceryl acetal, 1-p-menthen-9-ol, 1,2-dihydrolimonen-10-ol, 2,3,4-trimethyl-3-pentanol, 2,4-dimethylcyclohexylmethanol, 2-methyl-1-hepten-3-ol, 2-tert-butylcyclohexanol, 3-ethyl-3-octanol, 4-isopropylcyclohexanol, 5-hexenol, 5-octene-1,3-diol, 6-hydroxydihydrotheaspirane, 8-ethyl-1,5-dimethylbicyclo[3.2.1]octan-8-ol, cis-3-heptenol, cis-4-octenol, cyclododecanol, α-limonene-10-ol, d-trans,cis-1(7), 8-p-menthadien-2-ol, 3,7-dimethyl-1,6-nonadien-3-ol, linalool oxide (pyranoid), quercivorol, nerolidol oxide, nootkatol, p-menthan-3,8-diol, santalol, and tetrahydronootkatol.

In consideration of issues such as compatibility with the cell division inhibitor of a pyridine-based compound or a benzamide-based compound, the aliphatic alcohol having 6 to 20 carbon atoms is particularly desirably decyl alcohol, 2-ethylhexanol or geraniol.

The mixing ratio of the cell division inhibitor selected from pyridine-based compounds and benzamide-based compounds to the aliphatic alcohol having 6 to 20 carbon atoms is not particularly limited and is selected from a wide range depending on the combination of the selected cell division inhibitor and the aliphatic alcohol.

Although the inhibitor for tobacco axillary bud growth of the present invention may be used without adding any other components, the inhibitor is usually mixed with a solid carrier, a liquid carrier or a gas carrier, and as necessary, is further supplemented with a surfactant, an extender, a colorant, a binder, an antifreezing agent, an ultraviolet absorber, or the like, to be formulated into an oil solution, an emulsion, a solubilizer, a wettable powder, a suspension, a flowable agent, a powder, or the like before application.

The surfactant is not particularly limited, and examples thereof include a phenylphenolsulfonic acid-formaldehyde condensate, sodium dioctyl sulfosuccinate, a sodium alkylnaphthalene sulfonate, a polyoxyethylene alkyl phenyl ether, a sodium naphthalenesulfonate condensate, a sodium polyoxyethylene alkyl phenyl ether sulfoacetate, a ammonium polyoxyethylene alkyl phenyl ether sulfate, an ethylene oxide-propylene oxide copolymer, and an alkenyl sulfonate.

The extender is not particularly limited, and examples thereof include: plant powders such as soybean powder, tobacco powder, wheat powder, and wood powder; clay minerals such as clay, bentonite, acid clay, and radiolite; talcs such as talc powder and agalmatolite powder; mineral powders such as diatomaceous earth and mica powder; and sodium bicarbonate, calcium carbonate, alumina, and activated carbon.

The colorant is not particularly limited, and examples thereof include: inorganic pigments such as iron oxide, titanium oxide, and Prussian blue; organic dyes such as an alizarin dye, an azo dye, and a metallophthalocyanine dye; and trace elements such as iron, manganese, boron, copper, cobalt, molybdenum, and zinc.

The binder is not particularly limited, and examples thereof include carboxymethylcellulose sodium salt, starch, sodium lignin sulfonate, dextrin and polyvinyl alcohol.

The antifreezing agent is not particularly limited, and examples thereof include glycerin, ethylene glycol, and propylene glycol.

The ultraviolet absorber is not particularly limited, and examples thereof include substituted benzophenone, a diphenylacrylonitrile ester and a cinnamic acid ester.

The inhibitor for tobacco axillary bud growth of the present invention may be a mixture of the cell division inhibitor selected from pyridine-based compounds and benzamide-based compounds and the aliphatic alcohol having 6 to 20 carbon atoms formed by separately formulating both the components and appropriately mixing them before use.

For example, in the case of treating tobacco with the inhibitor for tobacco axillary bud growth of the present invention, it is recommended that the concentration of one or more kinds of active ingredients selected from the above-mentioned pyridine-based compounds and benzamide-based compounds be 0.001 to 0.1% by mass.

In addition, in the case of using the cell division inhibitor comprising at least one member selected from pyridine-based compounds and benzamide-based compounds in combination with the aliphatic alcohol having 6 to 20 carbon atoms, the mixing ratio of the cell division inhibitor to the aliphatic alcohol having 6 to 20 carbon atoms is usually 1:1,000 to 1,000:1, preferably 1:300 to 300:1 in terms of mass ratio.

As a tobacco (*Nicotiana tabacum*) cultivar which is suppressed by the inhibitor for tobacco axillary bud growth of the present invention in formation and elongation of axillary buds, there are given for example: domestic cultivars typified by Matsukawa, Daruma, Awa, and Siroenshu; flue-cured cultivars typified by Coker 319, Virginia 115, MC 1, Okinawa 2, Bright Yellow 4, Tsukuba 1, and Tsukuba 2; and burley cultivars typified by Burley 21, Kitakami 1, Michinoku 1 and Michinoku 2.

The use amount of the inhibitor for tobacco axillary bud growth of the present invention varies depending on the cultivar, method and timing of use, and the use amount of a spray solution per plant is desirably 5 to 40 ml, more desirably 15 to 30 ml.

In addition, with regard to the number of times of application of the inhibitor for tobacco axillary bud growth of the present invention, in the case where the first application is carried out before blooming of tobacco or before top pruning or in the case where tree vigor of tobacco is strong even after the first spraying after the top pruning, the inhibitor is effectively applied by performing the first application and subsequently the second spraying two weeks after the first application in the same manner as in the first application.

The inhibitor for tobacco auxiliary bud growth of the present invention may further contain known herbicides in order to enhance the efficacy. Examples of the herbicides include the following: ioxynil, aclonifen, aziprotryne, acifluorfen-sodium, azimsulfuron, asulam, atrazine, azafenidin, amicarbazone, amidosulfuron, amitrole, aminocyclopyrachlor, aminopyralid, amiprophos-methyl, ametryne, alachlor, alloxydim, isouron, isoxachlortole, isoxaflutole, isoxaben, isoproturon, imazaquin, imazapic, imazapyr, imazamethabenz-methyl, imazamox-ammonium, imazethapyr, imazosulfuron, indanofan, indaziflam, eglinazine-ethyl, esprocarb, ethalfluralin, ethametsulfuron-methyl, ethidimuron, ethoxysulfuron, ethoxyfen-ethyl, ethofumesate, etobenzanid, endothal disodium, oxadiazon, oxadiargyl, oxaziclomefone, oxasulfuron, oxyfluorfen, oryzalin, orthosulfamuron, orthobencarb, oleic acid, cafenstrole, carfentrazone-ethyl, carbetamide, quizalofop-ethyl, quinoclamine, quinclorac, quinmerac, cumyluron, clethodim, clodinafop-propargyl, clopyralid, clomazone, chlomethoxyfen, clomeprop, cloransulam-methyl, chloramben, chlorimuron-ethyl, DCBN, chlorphthalim, chloroxuron, chlorsulfuron, chlorthal-dimethyl, chlornitrofen, chlorbufam, chlorflurenol-methyl, chlorpropham, chlorbromuron, chlorotoluron, chloroacetic acid, Xanthomonas campestris, cyanazine, sodium cyanate, cycloate, cycloxydim, diclosulam, cyclosulfamuron, dichlorprop, DBN, diclofop-methyl, diquat-dibromide, siduron, dinitramine, cinidon-ethyl, cinosulfuron, dinoseb, dinoterb, cyhalofop-butyl, difenoxuron, difenzoquat, diflufenican, diflufenzopyr, dipropetryn, dimethametryn, dimethenamid, simetryne, dimepiperate, dimefuron, simazine, cinmethylin, sulcotrione, sulfentrazone, sulfosulfuron, sulfometuron-methyl, sethoxydim, terbacil, terbuthylazine, terbutryne, dymron, dazomet, terbumeton, dalapon, thiazafluron, thiencarbazone, tiocarbazil, thidiazimin, thifensulfuron-methyl, desmedipham, thenylchlor, tetrapion, tebuthiuron, tepraloxydim, tefuryltrione, desmetryne, tembotrione, topramezone, tralkoxydim, triaziflam, triasulfuron, tri-allate, trietazine, triclopyr, tritosulfuron, triofensulfuron, triflusulfuron-methyl, trifluralin, trifloxysulfuron-sodium, tribenuron-methyl, Drechsrela monoceras, naptalam, nicosulfuron, neburon, norflurazon, paraquat-dichloride, haloxyfop, halosafen, halosulfuron-methyl, bialaphos, picloram, picolinafen, bispyribac-sodium, pinoxaden, bifenox, pyrachlonil, pyrasulfotole, pyrazoxyfen, pyrazosulfuron-ethyl, pyrazolate, pyrazon, pyraflulfen-ethyl, pyridafol, pyrithiobac-sodium, pyridate, pyriftalid, pyributicarb, pyribenzoxim, pyrimisulfan, pyriminobac-methyl, pyroxasulfone, pyroxsulam, prometryne, fenuron, fenoxasulfone, fenoxaprop-ethyl, fentrazamide, phenmedipham, fosamine-ammonium, fomesafen, foramsulfuron, butachlor, butafenacil, butamiphos, butylate, butralin, butroxydim, flumetsulam, flazasulfuron, flamprop, primisulfuron-methyl, fluazifop, fluazolate, fluometuron, fluoroglycofen-ethyl, flucarbazone-sodium, fluchloralin, flucetosufuron, fluthiacet-methyl, flupyrsulfuron-methyl-sodium, flufenpyr-ethyl, flupoxam, flumioxazin, flumiclorac-pentyl, fluridone, flurenol, pretilachlor, proglinazine-ethyl, prodiamine, prosulfuron, propaquizafop, propazine, propanil, propisochlor, propyrisulfuron, propham, profoxydim, profluazol, prosulfocarb, propoxycarbazone-sodium, bromacil, prometon, bromoxynil, bromofenoxim, bromobutide, florasulam, fluroxypyr, flurochloridone, flurtamone, hexazinone, benazolin-ethyl, benefin, penoxsulam, beflubutamid, pebulate, pelargonic acid, vernolate, bencarbazone), benzfendizone, bensulide, bensulfuron-methyl, benzobicyclon, benzofenap, bentazon, pentanochlor, benthiocarb, pendimethalin, pentoxazone, benfuresate, mesosulfuron-methyl, mesotrione, methasulfocarb, methabenzthiazuron, metamitron, metamifop, metazosulfuron, metam, MSMA (methylarsonic acid), methiozolin, methyldymron, metoxuron, metosulam, metsulfuron-methyl, methoprotryne, metobromuron, metobenzuron, metolachlor/S-metolachlor, metribuzin, monosulfuron, monolinuron, molinate, iodosulfuron-methyl-sodium, lactofen, linuron, rimsulfuron, lenacil, DCMU (Diuron), sodium chlorate, 2,3,6-TBA (2,3,6-trichlorobenzoic acid), 2,4,5-T (2,4,5-trichlorophenoxyacetic acid), 2,4-DB (4-(2,4-dichlorophenoxy)butyric acid), 2,4-PA (2,4-Dichlorophenoxyacetic acid), DNOC (4,6-dinitro-O-cresol), EPTC (S-ethyl dipropylthiocarbamate), MCPA ((4-chloro-2-methylphenoxy)acetic acid), MCPB (4-(4-chloro-2-methylphenoxy)butryric acid), MDBA (dicamba), sodium-trichloroacetate, hexanoic acid, heptanoic acid, octanoic acid, decanoic acid, undecanoic acid, dodecanoic acid, trimethyl hexanoic acid, cedar essence oil, cedarwood oil, Japanese cypress oil, eucalyptus oil, clove oil, citrus oil and lemon oil.

Further, the inhibitor for tobacco auxiliary bud growth of the present invention may further contain other insecticides, bactericides, plant growth regulators, fertilizers and the like to expand the range of action.

EXAMPLES

Examples of the present inventions are described hereinafter.

Formulation examples are given first. The active ingredients, kinds of the additives and the compounding ratio thereof are not limited to the description set forth below and may be varied over a wide range. Here, the term "part(s)" means "part(s) by mass" in the following examples.

Formulation Example 1

An emulsion was obtained by dissolving 10 parts by mass of dithiopyr (manufactured by Wako Pure Chemical Industries, Ltd.) in 43 parts by mass of N-methylpyrrolidone, adding thereto 22 parts by mass of SAS 296 (tradename; manufactured by Nippon Petrochemicals) and 25 parts by mass of Sorpol 3880L (tradename; manufactured by TOHO CHEMICAL INDUSTRY Co., Ltd.) and stirring the mixture to be uniformly dissolved.

Formulation Example 2

A flowable formulation was obtained by mixing well 10 parts by mass of dithiopyr (manufactured by Wako Pure Chemical Industries, Ltd.), 11 parts by mass of propylene glycol, 3 parts by mass of Sorpol 7290P (tradename; manufactured by TOHO CHEMICAL INDUSTRY Co., Ltd.), 0.1 part by mass of ToxanonN100 (tradename; manufactured by Sanyo Chemical Industries, Ltd.), 0.2 parts by mass of Antifoam E-20 (tradename; manufactured by KAO Corporation), 1.5 parts by mass of Kunipia F (tradename; manufactured by Kunimine Industries Co., Ltd.) and 74.2 parts by mass of water; and pulverizing the mixture by a wet method till the particle size becomes 5 µm or less.

Formulation Example 3

An emulsion was obtained by dissolving 10 parts by mass of propyzamide (manufactured by Wako Pure Chemical Industries, Ltd.) in 43 parts by mass of N-methylpyrrolidone, adding thereto 22 parts by mass of SAS 296 (tradename; manufactured by Nippon Petrochemicals) and 25 parts by mass of Sorpol 3880L (tradename; manufactured by TOHO CHEMICAL INDUSTRY Co., Ltd.) and stirring the mixture to be uniformly dissolved.

Formulation Example 4

A flowable formulation was obtained by mixing well 10 parts by mass of propyzamide (manufactured by Wako Pure Chemical Industries, Ltd.), 11 parts by mass of propylene glycol, 3 parts by mass of Sorpol 7290P (tradename; manufactured by TOHO CHEMICAL INDUSTRY Co., Ltd.), 0.1 part by mass of ToxanonN100 (tradename; manufactured by Sanyo Chemical Industries, Ltd.), 0.2 parts by mass of Antifoam E-20 (tradename; manufactured by KAO Corporation), 1.5 parts by mass of Kunipia F (tradename; manufactured by Kunimine Industries Co., Ltd.) and 74.2 parts by mass of water; and pulverizing the mixture by a wet method till the particle size becomes 5 µm or less.

Test Examples

Next, Test Examples are described below, which tests were conducted to confirm the efficacy of the inhibitor for tobacco auxiliary bud growth of the present invention.

Test Example 1

Tobacco seedlings of Tsukuba 1 (flue-cured cultivar) and Michinoku 1 (burley cultivar) were transplanted to 1/5000a Wagner pots filled with Kureha garden nursery soil. The plants were grown in a glasshouse, and the floral axis parts were removed at the time of single-flower bloom of tobacco (top pruning).

The formulations of the inhibitors for tobacco axillary bud growth obtained in Formulation Examples 1 to 4 above were each diluted with water to predetermined concentrations, and 20 ml of the water-diluted solutions of the respective inhibitors were separately sprayed using a contact-type axillary bud inhibitor spraying instrument equipped with a spot exhaust nozzle (Examples 1 to 4 and 5 to 8). In addition, butralin (trade name: Blue Ribbon) (Comparative Examples 1 to 2 and 5 to 6) and decyl alcohol (trade name: Contact) (Comparative Examples 3 to 4 and 7 to 8) were used for tests as comparative examples in the same manner as above. In the cases of both the flue-cured cultivar and burley cultivar, one plant was planted per pot, and the tests were carried out in duplicate.

For the respective cases, states of inhibition of axillary bud growth 28 days after the spraying were investigated together with untreated groups sprayed with no inhibitor, and axillary bud growth inhibition ratios were calculated by the following equation.

Axillary bud growth inhibition ratio=(fresh weight of axillary buds per plant of untreated group−fresh weight of axillary buds per plant of treated group)÷(fresh weight of axillary buds per plant of untreated group)×100  [Math. 1]

Further, the presence or absence of the harmful effect of each inhibitor was evaluated in one of the following four categories depending on the degrees of growth inhibition, gangrene, change in color, deformation and the like of leaves (first to fourth leaves from the top).

Large: A severely harmful effect was observed.
Middle: A clearly harmful effect was observed.
Small: A slightly harmful effect was observed.
Absent: No harmful effect was observed.

For each of the examples, the axillary bud growth inhibition ratio and the presence or absence of the harmful effects of the inhibitor are shown in Table 1 (flue-cured cultivar) and Table 2 (burley cultivar).

TABLE 1

| | Test compound | Concentration of active ingredient (%) | Axillary bud growth inhibition ratio (%) | Harmful effect of inhibitor |
|---|---|---|---|---|
| Example 1 | Dithiopyr (Formulation Example 1) | 0.03 | 100 | Absent |
| Example 2 | Dithiopyr (Formulation Example 2) | 0.03 | 100 | Absent |
| Example 3 | Propyzamide (Formulation Example 3) | 0.03 | 100 | Absent |
| Example 4 | Propyzamide (Formulation Example 4) | 0.03 | 97 | Absent |
| Comparative Example 1 | Butralin | 0.03 | 44 | Absent |
| Comparative Example 2 | Butralin | 0.35 | 98 | Minor |
| Comparative Example 3 | Decyl Alcohol | 0.03 | 0 | Absent |
| Comparative Example 4 | Decyl Alcohol | 2.6 | 91 | Minor |

TABLE 2

| | Test compound | Concentration of active ingredient (%) | Axillary bud growth inhibition ratio (%) | Harmful effect of inhibitor |
|---|---|---|---|---|
| Example 5 | Dithiopyr (Formulation Example 1) | 0.03 | 100 | Absent |
| Example 6 | Dithiopyr (Formulation Example 2) | 0.03 | 99 | Absent |
| Example 7 | Propyzamide (Formulation Example 3) | 0.03 | 100 | Absent |
| Example 8 | Propyzamide (Formulation Example 4) | 0.03 | 98 | Absent |
| Comparative Example 5 | Butralin | 0.03 | 48 | Absent |
| Comparative Example 6 | Butralin | 0.35 | 97 | Absent |
| Comparative Example 7 | Decyl Alcohol | 0.03 | 0 | Absent |
| Comparative Example 8 | Decyl Alcohol | 2.6 | 94 | Absent |

Test Example 2

Formulation of Formulation Example 1 or Formulation Example 3 was diluted with water to predetermined concentrations and mixed with decyl alcohol (manufactured by Wako Pure Chemical Industries, Ltd.), 2-ethylhexanol (manufactured by Wako Pure Chemical Industries, Ltd.) or geraniol (manufactured by Wako Pure Chemical Industries, Ltd.) at predetermined concentrations, and the resultant was adjusted and used for tests (Examples 9 to 14 and 15 to 20). In addition, as comparative examples, the formulation of Formulation Example 1 or Formulation Example 3 diluted with water to predetermined concentrations (Comparative Examples 9 to 10 and 14 to 15) and decyl alcohol, 2-ethylhexanol or geraniol diluted with water to a predetermined concentration were used for tests (Comparative Examples 11 to 13 and 16 to 18).

The respective inhibitors were sprayed in the same manner as in Test Example 1, and states of inhibition of axillary bud growth 28 days after the spraying were investigated together with untreated groups sprayed with no inhibitor. Then, axillary bud growth inhibition ratios were calculated.

The results are shown in Table 3 (flue-cured cultivar) and Table 4 (burley cultivar).

TABLE 3

| | Test compound | Concentration of active ingredient (%) | Axillary bud growth inhibition ratio (%) |
|---|---|---|---|
| Comparative Example 9 | Dithiopyr | 0.005 | 75 |
| Comparative Example 10 | Propyzamide | 0.005 | 70 |
| Comparative Example 11 | Decyl Alcohol | 0.5 | 30 |
| Comparative Example 12 | 2-ethylhexanol | 0.5 | 21 |
| Comparative Example 13 | Geraniol | 0.5 | 26 |
| Example 9 | Dithiopyr + decyl alcohol | 0.005 + 0.5 | 100 (83) |
| Example 10 | Dithiopyr + 2-ethylhexanol | 0.005 + 0.5 | 97 (80) |
| Example 11 | Dithiopyr + geraniol | 0.005 + 0.5 | 100 (82) |
| Example 12 | Propyzamide + decyl alcohol | 0.005 + 0.5 | 100 (79) |
| Example 13 | Propyzamide + 2-ethylhexanol | 0.005 + 0.5 | 96 (80) |
| Example 14 | Propyzamide + geraniol | 0.005 + 0.5 | 98 (76) |

TABLE 4

| Test compound | Concentration of active ingredient (%) | Axillary bud growth inhibition ratio (%) |
|---|---|---|
| Comparative Example 14 | Dithiopyr | 0.005 | 78 |
| Comparative Example 15 | Propyzamide | 0.005 | 72 |
| Comparative Example 16 | Decyl Alcohol | 0.5 | 37 |
| Comparative Example 17 | 2-ethylhexanol | 0.5 | 28 |
| Comparative Example 18 | Geraniol | 0.5 | 32 |
| Example 15 | Dithiopyr + decyl alcohol | 0.005 + 0.5 | 100 (86) |
| Example 16 | Dithiopyr + 2-ethylhexanol | 0.005 + 0.5 | 100 (84) |
| Example 17 | Dithiopyr + geraniol | 0.005 + 0.5 | 99 (85) |
| Example 18 | Propyzamide + decyl alcohol | 0.005 + 0.5 | 98 (82) |
| Example 19 | Propyzamide + 2-ethylhexanol | 0.005 + 0.5 | 96 (80) |
| Example 20 | Propyzamide + geraniol | 0.005 + 0.5 | 96 (81) |

It should be noted that the values in parentheses in the Tables represent predicted values of the effects of inhibiting axillary bud growth of mixed agents (that is, compounds mixed as active ingredients), that is, expected values of additive effects. The expected values were calculated by the following Colby's equation (Colby. S. R.; "Calculating Synergistic and Antagonistic Responses of Herbicide Combinations" Weed, Vol. 15(1), 20-22, 1967).

Colby's equation: $E = x + y - x \cdot y / 100$ [Math. 2]

E: Axillary bud growth inhibition ratio in the case of using a mixture of active compound A (concentration a) and active compound B (concentration b) (theoretical axillary bud growth inhibition ratio)

x: Axillary bud growth inhibition ratio in the case of using active compound A at concentration a y: Axillary bud growth inhibition ratio in the case of using active compound B at concentration b In the case where a measured value determined in the above-mentioned test (axillary bud growth inhibition ratio) was larger than the expected value, a synergetic effect was expressed on activity to suppress axillary bud growth.

As shown in Tables 1 and 2, the inhibitors for tobacco axillary bud growth of the present invention exhibited inhibition ratios as high as 90% or more for each of the flue-cured cultivar and the burley cultivar, at lower concentrations than those of the control compounds. Further, all the inhibitors for tobacco axillary bud growth of the present invention exhibited no harmful effect (Examples 1 to 8).

In addition, as shown in Tables 3 and 4, all the measured values of the inhibitors for tobacco axillary bud growth including the aliphatic alcohol in combination (Examples 9 to 20) are larger than the expected values of the additive effects determined from the measured values of the agents including only one component (Comparative Examples 9 to 18), which shows that the inhibitors have synergistic effects.

As apparent from the above, the inhibitor for tobacco axillary bud growth of the present invention has high effects of inhibiting axillary bud growth as compared to existing inhibitors for tobacco axillary bud growth and is excellent in terms of sustained chemical efficacy. In addition, it has been proved that the inhibitor for tobacco axillary bud growth of the present invention is superior also from the standpoint of causing no harmful effect.

The invention claimed is:

1. An inhibitor for tobacco axillary bud growth, comprising, as an active ingredient a synergistically effective combination of
    one or more cell division inhibitors selected from the group consisting of dithiopyr, thiazopyr, propyzamide, tebutam and benzipram; and
    an aliphatic alcohol selected from the group consisting of decyl alcohol, 2-ethyl hexanol, and geraniol,
    wherein the inhibitor is effective at inhibiting axillary bud growth on a tobacco plant.

2. The inhibitor for tobacco axillary bud growth according to claim 1, wherein the cell division inhibitor is dithiopyr.

3. The inhibitor for tobacco axillary bud growth according to claim 1, wherein the cell division inhibitor is propyzamide.

4. A method for inhibiting tobacco axillary bud growth, comprising applying to a tobacco plant the inhibitor for tobacco axillary bud growth according to claim 1.

* * * * *